(12) United States Patent
Feldkhun (10) Patent No.: US 9,921,161 B1
(45) Date of Patent: Mar. 20, 2018

(54) STRUCTURED LIGHT ACTIVE LOCALIZATION MICROSCOPY

(71) Applicant: Daniel Feldkhun, Boulder, CO (US)

(72) Inventor: Daniel Feldkhun, Boulder, CO (US)

(73) Assignee: Daniel Feldkhun, Boulder, CO (US)

( * ) Notice: Subject to any disclaimer, the term of this patent is extended or adjusted under 35 U.S.C. 154(b) by 96 days.

(21) Appl. No.: 14/991,016

(22) Filed: Jan. 8, 2016

Related U.S. Application Data (60) Provisional application No. 62/101,297, filed on Jan. 8, 2015.

(51) Int. Cl.
| | | |
|---|---|---|
| *H01J 65/08* | (2006.01) |
| *G01N 21/64* | (2006.01) |
| *G02B 21/16* | (2006.01) |
| *G02B 21/36* | (2006.01) |

(52) U.S. Cl.
CPC ......... *G01N 21/6458* (2013.01); *G02B 21/16* (2013.01); *G02B 21/365* (2013.01)

(58) Field of Classification Search
CPC .............. G01N 21/6458; G01N 21/64; G01N 21/6428; G01N 15/1429; G01N 15/1456; G01N 2015/0038; G01N 21/6486; G02B 27/58; G02B 21/16; G02B 26/06; G02B 21/365
USPC ...................................................... 250/459.1
See application file for complete search history.

(56) References Cited

U.S. PATENT DOCUMENTS

| | | | |
|---|---|---|---|
| 4,621,911 A | 11/1986 | Lanni et al. | |
| 7,298,461 B2 | 11/2007 | Cremer et al. | |
| 8,217,992 B2 | 7/2012 | Bewersdorf et al. | |
| 8,531,650 B2 | 9/2013 | Feldkhun et al. | |
| 8,558,998 B2 | 10/2013 | Feldkhun et al. | |
| 8,848,200 B2 | 9/2014 | Feldkhun | |
| 2005/0059681 A1* | 3/2005 | Cremer .............. G01N 21/6428 514/260.1 |

(Continued)

OTHER PUBLICATIONS

Betzig, E., et al., "Imaging Intracellular Fluorescent Proteins at Nanometer Resolution", Science, vol. 313, No. 5793, (Sep. 15, 2006), pp. 1642-1645.

(Continued)

*Primary Examiner* — Taeho Jo
(74) *Attorney, Agent, or Firm* — Cooley LLP (57) ABSTRACT

Methods and systems are provided for estimating locations of sub-wavelength-sized emitters, which may be sparsely arrayed among inactive emitters, in one or more dimensions to synthesize a super-resolved image. The emitter emits light in response to structured illumination, which may be acousto-optically generated. The structured illumination is translated, and a detector, such as a camera pixel, senses the emitted linear or nonlinear response, producing a periodic signal. A processor computes a phase of the signal using phase shifting interferometry and uses it to estimate the emitter location with resolution finer than a quarter of the illumination wavelength. Modulation depth and/or amplitude of the signal may be used to estimate emitter size and/or evaluate location fidelity. Optical sectioning or extended depth of field may be provided by controlling spatial coherence of the illumination. Encoding and decoding emitter locations with non-periodic patterns is also described.

22 Claims, 4 Drawing Sheets

(56) References Cited

U.S. PATENT DOCUMENTS

| | | | | |
|---|---|---|---|---|
| 2007/0187632 | A1* | 8/2007 | Igarashi | A61B 5/0048 250/559.36 |
| 2009/0046298 | A1* | 2/2009 | Betzig | G01N 21/6445 356/521 |
| 2009/0135432 | A1* | 5/2009 | Betzig | G01N 21/6445 356/521 |
| 2011/0036996 | A1* | 2/2011 | Wolleschensky | G01N 21/6458 250/459.1 |
| 2011/0300490 | A1* | 12/2011 | Rachet | G02B 21/0032 430/322 |
| 2012/0018651 | A1* | 1/2012 | Hess | G01J 3/02 250/459.1 |
| 2012/0069344 | A1* | 3/2012 | Liu | G01B 9/04 356/450 |
| 2013/0176574 | A1* | 7/2013 | Sirat | G02B 21/0056 356/496 |
| 2013/0286181 | A1* | 10/2013 | Betzig | H04N 7/18 348/79 |
| 2013/0314717 | A1* | 11/2013 | Yi | G02B 21/0032 356/479 |
| 2014/0038201 | A1* | 2/2014 | Zhuang | G01N 21/6428 435/7.1 |
| 2014/0063194 | A1* | 3/2014 | Zhuang | G01N 21/6428 348/46 |
| 2014/0198198 | A1* | 7/2014 | Geissbuehler | G01N 21/6458 348/79 |
| 2015/0001422 | A1* | 1/2015 | Englund | G01N 21/6458 250/459.1 |
| 2015/0192510 | A1* | 7/2015 | Piestun | G01B 11/002 702/151 |
| 2015/0212308 | A1* | 7/2015 | Sirat | G02B 21/0072 250/459.1 |
| 2016/0077167 | A1* | 3/2016 | Heidmann | G01N 24/10 324/304 |
| 2016/0085062 | A1* | 3/2016 | Kalkbrenner | G02B 21/006 348/49 |
| 2016/0139048 | A1* | 5/2016 | Heidmann | G01N 21/63 250/459.1 |
| 2016/0252719 | A1* | 9/2016 | Liu | G01N 33/4833 348/49 |
| 2016/0312272 | A1* | 10/2016 | Barish | C12Q 1/6834 |

OTHER PUBLICATIONS

Brophy, C. P., "Effect of intensity error correlation on the computed phase of phase-shifting interferometry", J. Opt. Soc. Am. A, vol. 7, No. 4, (Apr. 1990), pp. 537-541.

Gustafsson, M. G. L., "Surpassing the lateral resolution limit by a factor of two using structured illumination microscopy", J. Microsc., vol. 198, Pt. 2, (2000), pp. 82-87.

Hell, S. W., et al., "Breaking the diffraction resolution limit by stimulated emission: stimulated-emission-depletion fluorescence microscopy", Optics Letters, vol. 19, No. 11, (Jun. 1, 1994), pp. 780-782.

Huntley, J. M. et al., "Shape measurement by temporal phase unwrapping: comparison of unwrapping algorithms," Meas. Sci. Technol., vol. 8, (May 1997), pp. 986-992.

Malacara, D., ed., "Optical Shop Testing", Chapter 14—Phase Shifting Interferometry, 3rd ed., New Jersey: Wiley-Interscience, (2007), pp. 547-664.

Neil, M. A. A., et al., "Method of obtaining optical sectioning by using structured light in a conventional microscope", Optics Letters, vol. 22, No. 24, (Dec. 15, 1997), pp. 1905-1907.

Rust, M. J., et al., "Sub-diffraction-limit imaging by stochastic optical reconstruction microscopy (STORM)", Nature Methods, vol. 3, No. 10, (Oct. 2006), pp. 793-796.

* cited by examiner

STRUCTURED LIGHT ACTIVE LOCALIZATION MICROSCOPY

CROSS-REFERENCES TO RELATED APPLICATION

This application claims the benefit under 35 U.S.C. 119(e) of U.S. Provisional Patent Application Ser. No. 62/101,297, entitled "STRUCTURED LIGHT ACTIVE LOCALIZATION MICROSCOPY" filed Jan. 8, 2015, the entire disclosure of which is incorporated herein by reference for all purposes.

BACKGROUND

Far-field optical super-resolution microscopy techniques may aim to resolve features in a specimen substantially smaller than the classical Abbe diffraction resolution limit. Typically, the specimen may be biological and the features of interest may be labeled with fluorescent molecules or quantum dots. Some super-resolution techniques such as Structured Illumination Microscopy (SIM) (see for example, Gustafsson, M. G. L., J. Microsc., vol. 198, pt. 2, 2000, incorporated herein by reference) may illuminate the specimen sequentially with phase-shifted periodically-structured light, sometimes formed by an image of a shifted grating, to convert spatial frequencies that are classically unresolvable to resolvable spatial frequencies through a process analogous to the Moiré effect, thereby surpassing the Abbe limit by up to a factor of 2 in an epi-fluorescence microscope, or in some cases more if the fluorescence response to the excitation is nonlinear.

Lateral modulation of the specimen with phase-shifted incoherent structured illumination may also be utilized to reject background light and improve optical sectioning in a wide-field microscope (see, for example, Neil, M. A. A., Juskaitis, R. and Wilson, T., Optics Letters, vol. 22, 1997, incorporated herein by reference), whereas axially-varying structured illumination generated at the specimen by opposing microscope objectives may be used to improve depth resolution beyond the classical limit imposed by the diffraction-limited depth of field. For example, in Spatially Modulated Illumination (SMI) microscopy, disclosed in U.S. Pat. No. 7,298,461, incorporated herein by reference, a sub-wavelength sized fluorescent object moved axially through an apodized structured illumination field between two opposing objectives may produce a modulated detector signal, which may be fitted to a function to estimate the emitter's size and distance with respect to other emitters in the field with a resolution exceeding the classical limit.

Other super-resolution techniques, such as Stimulated Emission Depletion (STED) microscopy (see Hell, S. W., Wichmann, J., Optics Letters, vol. 19, no. 11, 1994, incorporated herein by reference) may improve resolution further by exploiting a non-linear fluorescence excitation process. In STED, for example, the specimen may be scanned with a doughnut-shaped focal spot temporarily depleting fluorescence of specialized fluorophores outside a small central spot, which may be much smaller than the Abbe limit. The undepleted fluorophores within the spot may then be measured and localized using a conventional focused excitation beam at a different wavelength.

Other super-resolution approaches may exploit stochastic properties of fluorescence to isolate and localize individual fluorophores with precision exceeding the Abbe limit. For example, Photoactivated Localization Microscopy (PALM) (see Betzig, E. et al., Science, vol. 313, no. 5793, 2006, incorporated herein by reference) and Stochastic Optical Reconstruction Microscopy (STORM) (see Rust. NI, J., Bates, M., Zhuang, X., Nature Methods, vol. 3, no. 20, 2006, incorporated herein by reference) employ photoswitchable fluorescent molecules, the majority of which are in a dark state at any given time and do not fluoresce in response to an excitation laser. However, a weak activation laser at another wavelength (or in some cases the same excitation laser) may be used to temporarily switch a small fraction of the molecules into an active state stochastically, resulting in a sparse distribution at any given time of mutually-isolated molecules which may fluoresce in response to the excitation laser. An image of the sparsely-distributed fluorescing molecules formed on a camera may be used to find their locations by estimating the centers of the respective point spread functions (PSFs) with a precision which may be substantially finer than the size of the PSF or the size of a pixel. After a short time, an active molecule may re-enter the dark state, may photobleach, or may be deactivated with another laser, while a new molecule may become active.

Localizations of different sparse sets of active molecules using a sequence of images may be combined to form a super-resolved image of the specimen if the density of fluorophores is sufficient to adequately sample the labeled features of interest. Localization precision may be limited by various factors such as the number of photons emitted from each molecule, background fluorescence, and the number of pixels sampling the PSF. In some cases, nine or more pixels may be needed to sufficiently localize a focused PSF distribution at the image plane, which may limit the measurement field of view, and/or acquisition speed. Furthermore, some activated molecules may reside outside the depth of field of the imaging system and their images may appear out of focus, requiring even more pixels for localization, limiting localization precision, and contributing background noise to in-focus emitter images. Auto-fluorescence from the specimen volume and residual fluorescence from de-activated molecules may compound background noise and further degrade attainable resolution.

SUMMARY

Embodiments of the present technology include techniques for single-molecule super-resolution microscopy with improved localization precision for in-focus and out-of-focus emitters. Examples of these techniques provide depth sectioning capability, suppress background noise, and/or reduce the number of camera pixels needed for localization.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1 illustrates a system and methods for estimating locations of one or more active microscopic emitters distributed among inactive emitters in a specimen along one dimension. During a locating time interval, the specimen is illuminated with an incrementally shifted periodic excitation pattern, causing the active emitters to emit modulated response radiations which are detected by corresponding elements in a detector array. The resulting modulated detector signals are processed using a phase shifting interferometry (PSI) process to estimate the phases of the modulations, from which the locations of the emitters can be computed with a precision substantially finer than the spatial period of the excitation pattern. The localization measurement is repeated for different sets of active emitters over different locating time intervals, and a super-resolved reconstruction of the specimen is constructed using the accumulated estimated emitter locations.

FIG. 2 illustrates estimating locations of active emitters in two-dimensions. Active emitters are sparsely interspersed among inactive emitters in a two-dimensional specimen illuminated by a sequence of orthogonally-directed incrementally-shifted periodic excitation patterns, which may have different periods. Response radiations from the active emitters are detected by a two-dimensional pixel array. For a given active emitter, each shifted pattern produces a modulated signal at the corresponding pixel. As in FIG. 1, the phases of the modulated signals due to each orthogonal pattern are estimated using a PSI process, and locations of the emitter along the orthogonal directions are computed by a processor. Location estimates of different sets of active emitters over multiple locating time intervals are combined to synthesize a super-resolved two-dimensional reconstruction of the specimen.

DETAILED DESCRIPTION

This description provides example embodiments only, and is not intended to limit the scope, applicability, or configuration of the disclosed technology. Rather, the ensuing description of the embodiments will provide those skilled in the art with an enabling description for implementing embodiments of the disclosed technology. Various changes may be made in the function and arrangement of elements without departing from the spirit and scope of the disclosed technology.

Thus, various embodiments may omit, substitute, or add various procedures or components as appropriate. For instance, it should be appreciated that in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner.

It should also be appreciated that the following systems, methods, and software may individually or collectively be components of a larger system, wherein other procedures may take precedence over or otherwise modify their application. Also, a number of steps may occur before, after, or concurrently with the following embodiments.

Figure 1:
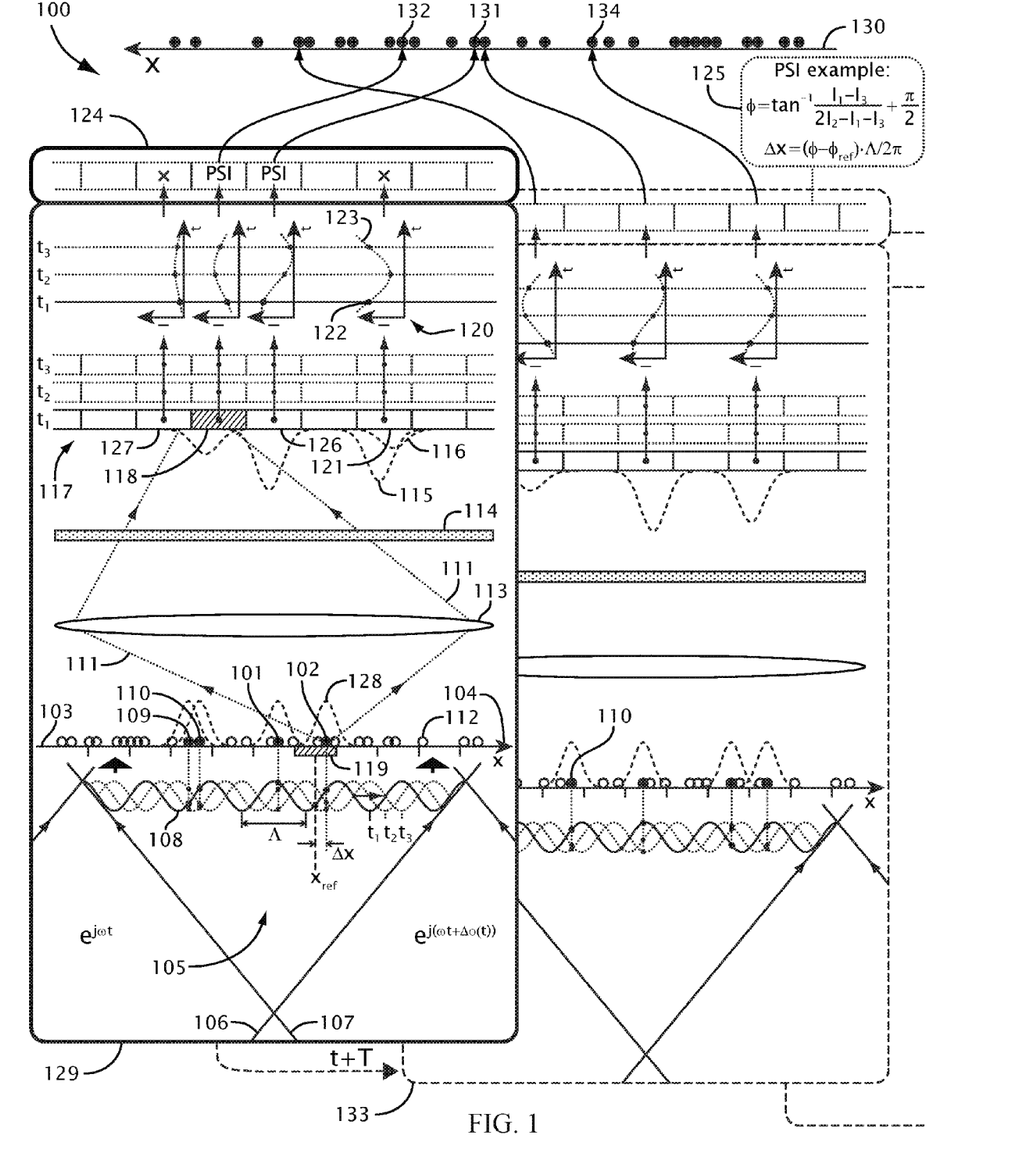

FIG. 1 illustrates a system 100 for estimating a location of one or more microscopic emitters, such as emitters 101 and 102 in a specimen 103 along a direction 104. The specimen and other features in FIG. 1 are depicted as one-dimensional merely for clarity of illustration and the concepts illustrated in the figure may be directly extended to multiple dimensions, as should be understood by those skilled in the art. In system 100, the specimen 103 is illuminated with an excitation radiation 105 with a wavelength $\lambda$ in the medium of the specimen, the excitation comprising two coherent beams 106 and 107 producing a periodic interference pattern 108 at the specimen with a spatial period $\Lambda$. In system 100, the emitters 101 and 102 are part of a sparse array of active emitters 101, 102, 109, and 110, which emit a response radiation, such as response radiation portion 111 from emitter 101, in response to the excitation radiation 105 during a locating time interval T In some embodiments, the excitation and response radiations may have different wavelengths. Within the specimen 103, the active emitters may be interspersed among inactive emitters, such as emitter 112, which do not respond to the excitation radiation 105 during the locating time interval T.

In some embodiments, the emitters may be fluorophores or quantum dots attached to or interacting with other features in the specimen, such as biological molecules or structures. In some embodiments emitters may be stochastically activated for a limited duration through photoswitching, photoconversion, or other processes using a separate activation illumination or the excitation radiation 105 itself, and later deactivated by entering a dark state or by photobleaching, as may occur in PALM, STORM, and other localization microscopy methods which may be known to those skilled in the art. In such embodiments some inactive emitters during a particular locating time interval may be active emitters during another locating time interval, and vice-versa. In some embodiments certain types of fluorophores, such as Alexa Fluor 647, may repeatedly activate, fluoresce, and deactivate stochastically in response to light from a single illumination source at a fixed wavelength without a separate activation or deactivation source.

In system 100, a portion of the response radiation emitted by the active emitters, such as response radiation portion 111 from emitter 101, may be collected by a lens 113, filtered by a filter 114 from the excitation radiation 105, and directed to form images of the active emitters, such as images 115 and 116, on a detector array 117. Each element of the detector array, such as element 118, may receive radiation predominantly from a corresponding region of the specimen, such as region 119. Each detector element may produce a signal due to the detected portion of the response radiations, such as signal 120 produced by detector element 121 due to images 115 and 116 formed on the detector element by response radiations from active emitters 109 and 110. In some embodiments, the detector array 117 may be a CCD or CMOS pixel array in a camera, or an array of avalanche photodiodes (APD), silicon photomultipliers (SIPM), or single photon avalanche diodes (SPAD), positioned in an image plane of a microscope.

The periodic interference pattern 108 may be translated with respect to the specimen 103 during the locating time interval, thereby exciting the active emitters with a time-varying intensity and producing a time-varying modulation of the detector signal. In system 100 the detector array elements may be read out to convert a sequence of exposures to the response radiations into corresponding intensity values, such as value 122, at discrete times, such as times $t_1$, $t_2$, and $t_3$, which may be on the time scale of milliseconds or faster in some embodiments, and the interference pattern 108 may be translated incrementally and synchronously with the detector read out, and may remain substantially stationary with respect to the specimen during each detector array exposure time. The interference pattern may be translated by incrementally imparting a phase offset Δϕ on one of the interfering beams 107 using a phase modulator such as a piezoelectrically-actuated mirror, a liquid crystal modulator, or an acousto-optic cell, for example. The incrementally-shifted excitation interference pattern may produce detector signal intensity values, such as value 122, which temporally sample a periodic function, such as function 123.

In system 100, for a given detector element, such as element 121, a Phase Shifting Interferometry (PSI) technique such as one of a variety of PSI techniques (see, for example, Malacara, D., ed. "Optical Shop Testing", 3$^{rd}$ ed., Wiley-Interscience, 2007, and U.S. Pat. No. 8,531,650, both incorporated herein by reference) or other PSI techniques which may be known to those skilled in the art, may be applied to the detector element signal 120 by a processor 124 to estimate the phase φ, amplitude, offset, and/or modulation depth of the periodic function 123, from the corresponding intensity values, such as value 122. The PSI technique may be used to estimate the phase of the periodic function 123 unambiguously within a range between 0 and 2π.

For a detector element receiving response radiation primarily from a single emitter substantially smaller than the period Λ of the interference pattern, such as detector element 118 receiving response radiation from emitter 102, the phase φ at a chosen time, such as time $t_1$, computed by the PSI technique may be used to estimate the relative location Δx of the emitter with respect to a reference, such as the center of the region 119 of the specimen 103 corresponding to the detector element 118, assuming the phase $\varphi_{ref}$ of the interference pattern at the reference location $x_{ref}$ at the chosen time $t_1$ is known: $\Delta x = (\varphi - \varphi_{ref}) \cdot \Lambda / 2\pi$.

For example, a simple PSI technique using three π/2 phase shifts of the interference pattern and three corresponding detector intensity values $I_1$, $I_2$, and $I_3$, to estimate the phase of the periodic function, such as function 123, as well as a method to convert the phase estimate to a location of the emitter is shown in box 125, and may be known as a three-step technique to those skilled in the art, however other N-step PSI techniques may be used as well. Bias b, amplitude a, and modulation depth m of the function 123 may be easily computed from the same data, as known to those skilled in the art. For example, by using a 5-step Schwider/Hariharan technique with π/2 phase steps, these quantities may be computed as follows: $\varphi = \tan^{-1}(2(I_2-I_4)/(2I_3-I_1-I_5))$, $b=(I_1+I_5+2(I_2+I_3+I_4))/2$, $a=2\sqrt{(4(I_4-I_2)^2+(I_1+I_5-2I_3)^2)}$, and $m=a/(2b)$. The phase φ may be computed unambiguously within a range spanning 2π using a 4-quadrant inverse tangent.

Under conditions with highly accurate, repeatable, and linear phase shifting and a large photon flux, PSI techniques may provide phase resolution as small as Λ/1000, for example. For some N-step PSI techniques, the standard deviation of the phase measurement may be approximated as $\sigma_\varphi \approx \sqrt{2}/(mS\sqrt{N})$, where $m=(I_{max}-I_{min})/(I_{max}+I_{min})$ is the modulation depth and S is the signal-to-noise ratio of the detector signal (see Brophy, C. P., J. Opt. Soc. Am. A, vol. 7, no. 4, 537-541, 1990, incorporated herein by reference). In a shot-noise-limited measurement, S may be approximated as $S \approx \sqrt{n}$, where n is the mean number of photons detected during the detector exposure time, resulting in a standard deviation of the emitter location of $\sigma_x = \Lambda \cdot \sigma_\varphi/(2\pi) \approx \Lambda/(\pi\sqrt{(2Nn)})$ for a fully-modulated signal with m=1. For example, for a 5-step PSI technique, with 100 photons detected on average during each step from a single fluorescing emitter, and Λ=250 nm (assuming ~500 nm excitation and an illumination numerical aperture NA=1), emitter localization precision may be as fine as ~2.5 nm. Emitter localization precision may be substantially higher than the classical diffraction-limited resolution width of the image-forming system, which estimates the minimum resolvable separation of two point spread functions (PSFs), such as PSF 128, at the specimen. In some embodiments, localization precision may be substantially finer than a quarter of the excitation wavelength λ. Merely by way of example for reference, with an excitation wavelength λ=500 nm and an imaging system NA=1, the diffraction-limited resolution may be ~λ/2≈250 nm.

The localization precision estimate exemplified above depends, however, on various assumptions, and in practice uncertainties of the phase estimate and resulting location estimate of the emitter may be higher. In some embodiments, localization precision and accuracy may be affected by quantization of the detector signal, systematic errors in phase-stepping the interference pattern 108, background emission indistinguishable from the response radiation which may reduce the modulation depth, or nonlinearities in emitter response to the excitation radiation 105, for example. Some PSI techniques are more sensitive to such potential error sources than others and those skilled in the art may choose a PSI technique which is most tolerant to known sources of errors in the system. This may come with the cost of additional phase steps and detector exposures needed during the locating time interval. For example, an technique requiring 5 π/2 phase shifts of the interference pattern 108, known to some as the Schwider or Hariharan technique (see Malacara, D., ed. "Optical Shop Testing", 3rd ed., Wiley-Interscience, 2007, incorporated herein by reference), may be more tolerant to phase stepping errors and/or nonlinear emitter response than the faster 3-step technique shown in box 125.

In the localization precision calculations above it is also assumed that the detector element receives response radiation from a single point-like emitter with a size much smaller than the period of the excitation interference pattern 108. In practice, the detector element, such as element 121, may be exposed to images, such as images 115 and 116, of and thereby receive portions of response radiations from two or more emitters, such as emitters 109 and 110. In such cases, the modulation depth of the periodic function 123 sampled by the corresponding detector signal 120 may be reduced, leading to an increased localization uncertainty, and the estimated location may be a mean of the locations of the contributing emitters 109 and 110 weighted by the relative portions of their response radiations contributing to the detector signal. In some embodiments, the modulation depth may be used to estimate a confidence level of the localization of the emitter, which may be used to reject the location estimate or assign error bars to it, for example. In some cases, a single emitter may not be point-like and its size may not be small compared to the period Λ of the excitation pattern 108. Such a relatively-large emitter may be considered as a combination of multiple point-like emitters as discussed above. For example, an emitter with a size of Λ/2 may reduce the modulation depth by 33%, increasing the uncertainty in the localization of its center by a factor of ~1.5, whereas an emitter with a size of Λ may not produce any modulation at all. In some embodiments the modulation depth may be used to estimate a size of the emitter.

In some cases where only a single emitter, such as emitter 102, is found in the specimen region corresponding to a detector element, such as element 118, a portion of the image of another emitter, such as emitter 101, primarily incident on a nearby detector element, such as element 126, may contribute to the signal of detector element 118, reducing its modulation depth and affecting its phase, thereby introducing an error in the phase and location estimation of emitter 102 through crosstalk. In other cases a detector element without a corresponding emitter in the specimen, such as element 127, may receive a small portion of the image incident on a nearby detector element, such as element 118, resulting in a weak modulation and potentially producing a location estimate of a "ghost" emitter within the specimen region corresponding to element 127 that is not actually there. Relatedly, in some embodiments in which a detector element may be able to receive response radiation from a region in the specimen 103 spanning more than one period of the excitation interference pattern 108, there may be an ambiguity of Λ in the location of the emitter.

Advantageously, the processor 124 may reject false or questionable localizations based on the modulation depth, bias, and/or amplitude of the detector element signal, as well as correspondences between the phases of signals of nearby detector elements. For example, the processor 124 may identify signal 120 as being due to two emitters based on a larger signal bias and reduced modulation depth compared to other detector elements. The processor may be programmed to discard such multiple-emitter location data as illustrated in FIG. 1. In the example case of detector element 127 being exposed to a small portion of the image of emitter 102, the processor may reassign the weak signal from detector element 127 to element 118 based on the relative strength and phasing of the two signals, thereby avoiding localizing of a "ghost" emitter as described above. The processor may also process images of the emitters sampled by the detector array, which may be separately acquired with spatially-uniform excitation illumination or synthesized from the modulated detector signals, for example. The processor may use such sampled images to identify and estimate crosstalk between neighboring detector elements and to reassign signal portions from one detector element to another to eliminate or reduce emitter location errors due to crosstalk.

In some embodiments the occurrences of multiple-emitter signals, crosstalk, "ghosting", and location ambiguities as described above may be eliminated or reduced by controlling the sparsity of active emitters and choosing the detector element size with respect to the imaging magnification and interference pattern period Λ to ensure that statistically during the locating time interval, each detector element is likely to receive response radiation from only a single emitter located within a region on the specimen smaller than Λ As may be the case in PALM and STORM microscopy, for example, the sparsity of active emitters may be controlled by the intensity of an activation radiation. To optimize localization precision while minimizing crosstalk, "ghosting", and location ambiguities, in some embodiments it may be advantageous to choose Λ to be as small as possible while being larger than the width of the optical point spread function (PSF) at the specimen, such as PSF 128, and to choose a detector element size to be the largest size for which the corresponding region on the specimen, such as region 119, is smaller than Λ when convolved with the PSF at the specimen, for example. In some embodiments, Λ may be chosen to span two or more detector element regions, such as region 119, so that the interference pattern may be resolved by the detector array, and the phase shifts may be calibrated and registered with respect to the specimen.

In some embodiments, active emitter location estimates computed and not rejected by the processor 124 from detector signals acquired during a measurement 129 spanning a locating time interval T may be used to populate a reconstruction 130 of the specimen 103 with representations, such as representations 131 and 132, of the emitters, such as emitters 101 and 102. The emitter representations may be point-like, of uniform size, or in some embodiments may be sized based on the amplitude and modulation depth of the corresponding signals to reflect an estimated spatial extent of the one or more emitters contributing to the signal. Location estimates from detector signals acquired during measurements, such as measurement 133, spanning other locating time intervals may be used to populate other locations of the reconstruction, such as location 134, thereby sequentially synthesizing an increasingly dense reconstruction 130 of the specimen 103.

In some embodiments with sufficient density of active and inactive emitters the resolution of the synthesized reconstruction 130 may be substantially higher than the classical diffraction-limited resolution of the imaging system. In some embodiments the resolution of the synthesized reconstruction may be limited by the density of active and inactive emitters in the specimen 103. Sometimes an emitter may remain active over multiple locating time intervals, such as emitter 110. In some embodiments it may be unlikely for two nearby emitters to activate and deactivate concurrently and it may be possible to estimate the location of an active emitter, such as emitter 110, which may be too close to another active emitter during another locating time interval.

Sometimes an emitter may deactivate before a location measurement is completed. In such embodiments, a drop in the detector signal may be detected and the resulting incorrect location estimate may be rejected by the processor 124.

It should be apparent to those skilled in the art that FIG. 1 represents just one of many possible embodiments. The excitation radiation 105 may be coherent and may form an interference pattern 108 which may be translated by phase-shifting one of the interfering beams as shown, or it may be partially coherent and may form an image of a periodic structure which may be physically or electronically translated to shift the excitation radiation distribution at the specimen. In some embodiments the periodic structure may be created using a liquid crystal or micro-mirror based spatial light modulator, or using an acousto-optic device, for example. In some embodiments, partially-coherent excitation radiation producing a periodic excitation pattern with a limited depth of field may be used to reject response radiation from emitters outside of a focal plane of interest by applying a modulation depth filter to the detector signals, for example.

In some embodiments the emitters may be fluorescent, producing a response radiation at a different wavelength than the excitation radiation wavelength, and one or more spectral filters may be used in the optical path leading to the detector to pass the response radiation and block the excitation radiation. In other embodiments, the emitters may comprise particles coherently scattering the excitation radiation, and other methods to substantially block the excitation radiation from reaching the detector, such as dark-field illumination, may be employed.

In some embodiments, methods of FIG. 1 may be applied to the signal from a single detector element or a single-element detector to locate one or more emitters within a given field of view, without a detector array. In some embodiments it may be possible to locate an emitter without forming an image of the emitter at the detector element using methods of FIG. 1, as long as the detector element is positioned to detect a portion of the modulated response radiation from the emitter. While FIG. 1 illustrates a discrete set of shifts of the interference pattern and the detected intensity values, in some embodiments the translation of the excitation pattern and/or the detector signals may be continuous. For example, the interference pattern may be translated rapidly and continuously using an acousto-optic device and the emitter response may be detected using one or more high-speed detectors such as an avalanche photodiode or a photomultiplier. In some embodiments the phase of the detector signal may be estimated by other methods than PSI, such as by a Hilbert transform or a Fourier transform of the detector signal.

In some embodiments, instead of translating the excitation pattern by phase shifting, the spatial frequency of the pattern may be changed to produce a periodic modulation at the detector. The phase of the modulation may be computed using a PSI technique, as in the case of phase shifting. However, in such embodiments the frequency of the modulation may vary from location to location. In some embodiments, the location-dependent modulation frequency may be utilized to disambiguate the location of the emitter over a range spanning multiple periods of the illumination, as may be effected in various embodiments of FIG. 6, of U.S. Pat. No. 8,531,650, incorporated herein by reference, for example.

In some embodiments the excitation radiation 105 may be strong and the emitter response may be nonlinear. In some embodiments the excitation pattern may not be sinusoidal as shown and may comprise higher harmonics. In some embodiments, PSI techniques may be chosen which may accurately estimate phase in the presence of nonlinearities. In some embodiments the processor 124 may separate a nonlinear detector signal into its harmonic components and estimate the phases of one or more higher harmonics to further improve localization precision.

The spatial period $\Lambda$ of the excitation radiation may be larger or smaller than illustrated. For example, in some embodiments $\Lambda$ may be as small as one half of the excitation wavelength in the medium of the specimen, whereas in other embodiments $\Lambda$ may be larger than the detector field of view. In some embodiments the excitation response may be nonlinear and $\Lambda$ may be a harmonic fraction of the excitation intensity variation period. For example, in the case of two-photon excitation of a fluorophore, two photons may need to arrive at the emitter substantially simultaneously in order to provide sufficient energy to excite the fluorophore. In this case, the emitter may respond to the incident intensity squared, thus doubling the spatial frequency of the excitation, so that the effective $\Lambda$ used for locating the emitter may be half of the linear intensity variation period and may be as small as a quarter of the wavelength of incident illumination in the medium of the specimen. In some embodiments, a detector element may be positioned to detect response radiations from one or more emitters located in a region of the specimen spanning more than one period $\Lambda$, and spatial variations in the excitation pattern or illumination with multiple spatial periods may be used to disambiguate their locations, as may be understood by those skilled in the art.

In some embodiments where the emitter response may depend on wavelength or polarization of the excitation radiation, the distribution of the excitation radiation at the specimen may vary in wavelength or polarization instead of amplitude, for example.

The simplified one-dimensional optical arrangement in FIG. 1 is intended merely for illustration. In some embodiments, the specimen may be positioned under an objective lens of a microscope and the detection and illumination optical paths may comprise additional lenses, filter elements, as well as viewing and imaging ports, for example. In some embodiments the detector array may comprise one or more cameras, which may be positioned to sense different portions of the specimen or may be located in different conjugate image planes for depth sectioning, for example. In some embodiments, a single objective lens may be utilized to both illuminate the specimen with the excitation radiation and to collect the response radiation, as in epi-fluorescence microscopy.

The methods of FIG. 1 may be applied to multi-dimensional specimens and the detector array and/or image reconstruction may be multi-dimensional. While the illustrated locating direction is lateral, in some embodiments the excitation pattern may vary and the emitter locations may be estimated along other directions, such as an axial direction with respect to the imaging system. In some embodiments the illustrated methods may be applied to three-dimensional localization.

Figure 2:
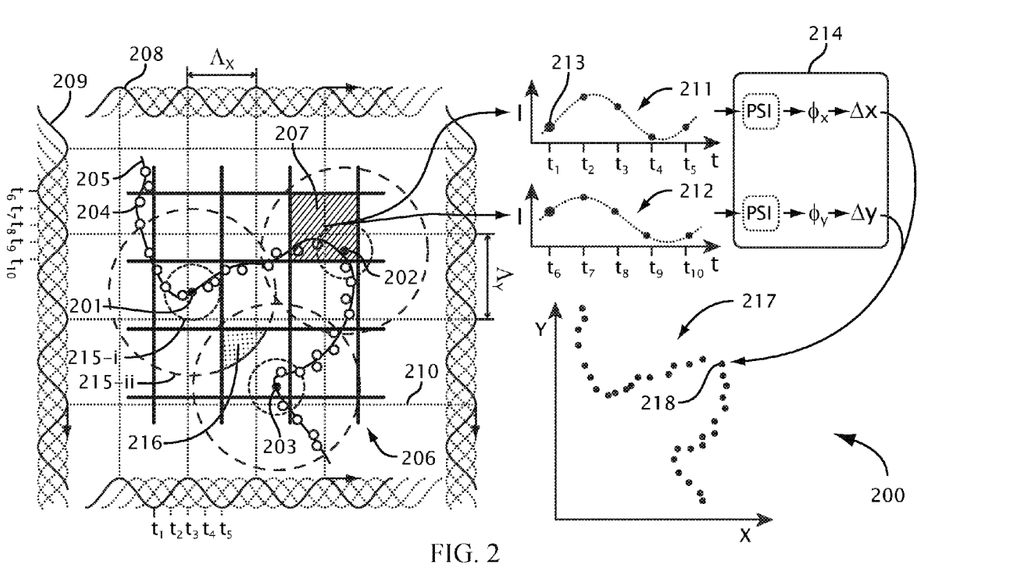

FIG. 2 illustrates a system 200, which may be a two-dimensional embodiment of system 100, for estimating a location of one or more microscopic emitters, such as sparsely arrayed active emitters 201, 202, and 203 interspersed among inactive emitters, such as emitter 204, attached to a structure 205 in a two-dimensional specimen. The structure 205 may be a filament in the cytoskeleton of a biological cell, for example. The active emitters may produce a response radiation during a locating time interval T in response to illumination of the specimen with an excitation radiation periodically distributed along two orthogonal directions, which may coincide with the principal axes of a two-dimensional array of detector elements, which may comprise pixels of a camera, for example.

FIG. 2 shows a mapping 206 of the pixel array on the specimen, where each rectangular region of the specimen, such as region 207, is mapped onto a separate pixel by an optical system such as the lens 113 of FIG. 1. The periodic distributions of excitation radiation along the orthogonal axes are illustrated by projections 208 and 209 with the locations of their crests on the specimen represented by dotted lines, such as line 210. As in system 100 of FIG. 1, each orthogonal excitation distribution is translated with respect to the specimen along the respective direction of variation in synchrony with the readout of the detector array to produce two modulated detector signals, such as signals 211 and 212 for region 207, for each translation direction, the detector signals comprising intensity values such as value 213.

The specimen may be illuminated with the orthogonal excitation radiation distributions 208 and 209 sequentially, producing two sequential detector signals, such as signals 211 and 212, such that at any given time t the excitation radiation distribution may vary spatially only along a single direction. In some embodiments, the orthogonal excitation patterns and resulting detector intensity values may be interleaved by alternating the excitation radiation illuminating the specimen between patterns 208 and 209 for each translation step. In other embodiments, the orthogonal excitation patterns 208 and 209 may vary with different spatial periods $\Lambda_x$ and $\Lambda_y$, may illuminate the specimen simultaneously, and a processor 214 may recover the detector signals due to each orthogonal pattern from a combined signal by spectral analysis.

As in system 100 of FIG. 1, in system 200 the processor 214 may estimate the phase of the signal, such as signals 211 and 212, due to each translated excitation distribution using PSI and determine the spatial offsets $\Lambda x$ and $\Lambda y$ of the corresponding emitter, such as emitter 202, along each direction with respect to the center of a pixel's field of view, such as region 207, or another known reference location.

As in system 100 of FIG. 1, in system 200 localization precision may be affected by multiple-emitter signals, crosstalk, "ghosting", and location ambiguities, which can be alleviated by an appropriate choice of active emitter sparsity, pixel size, and fringe period, as well as through filtering and signal reassignment based on signal modulation depth, amplitude and inter-pixel correlations. FIG. 2 uses concentric dotted circles, such as circles 215-i and 215-ii, to show the a and 2 σα contours, respectively, of the Gaussian approximation of the imaging Point Spread Function (PSF) for each active emitter. Region 216 illustrates crosstalk in the case of closely-spaced emitters and/or large pixels in two dimensions, which may affect the accuracy and precision of the location estimate of emitter 203 without additional processing.

In some embodiments, an image of the specimen formed on the pixel array may be used to estimate the locations of the emitter centers, identify regions of crosstalk, such as region 216, and reapportion detected intensity values between pixels to mitigate crosstalk by assigning a model of the imaging PSF, such as a Gaussian function, to each estimated emitter center location and computing the expected contribution of the emitter image to neighboring pixels. For example, the computed contribution of the image of emitter 201 to intensity detected from region 216 may be subtracted by the processor 214 from the total intensity detected by the corresponding pixel before the PSI technique is applied to the signal from that pixel. In some embodiments, this method for reducing crosstalk may be applied separately for each read out of the pixel array 206 and corresponding shift of the excitation radiation 208 or 209.

As in system 100 of FIG. 1, in system 200 super-resolved location estimates of individual emitters active during different locating time intervals T may be used to sequentially populate a two-dimensional reconstruction 217 of the structure 205 with point-like or extended representations of individual emitters, such as representation 218 of emitter 202. With sufficient density of active and inactive emitters to sample the features of interest according to the Nyquist criterion, a super-resolved image may thereby be synthesized.

It should be apparent to those skilled in the art that FIG. 2 represents just one of many possible embodiments. In some embodiments the directions of spatial variation of the excitation radiation may not coincide with the principal axes of the pixel array, and a coordinate transformation may be utilized to synthesize an image in pixel coordinates. In some embodiments, the directions variation and/or translation may not be orthogonal, while still providing the ability to localize emitters in two dimensions. In some embodiments, the periods $\Lambda_x$ and $\Lambda_y$ may be matched. In some embodiments the array of detector elements may comprise an APD, SPIM, or SPAD array instead of a CCD or CMOS pixel array. The 5-step PSI process is illustrated in FIG. 2 merely by way of example. The 3-step technique of FIG. 1 or a variety of other PSI processes may instead be used for phase estimation along each direction. In some embodiments, the specimen may be located under the objective lens of a microscope and the pixel array may comprise a camera positioned at a conjugate image plane of the microscope.

Figure 3:
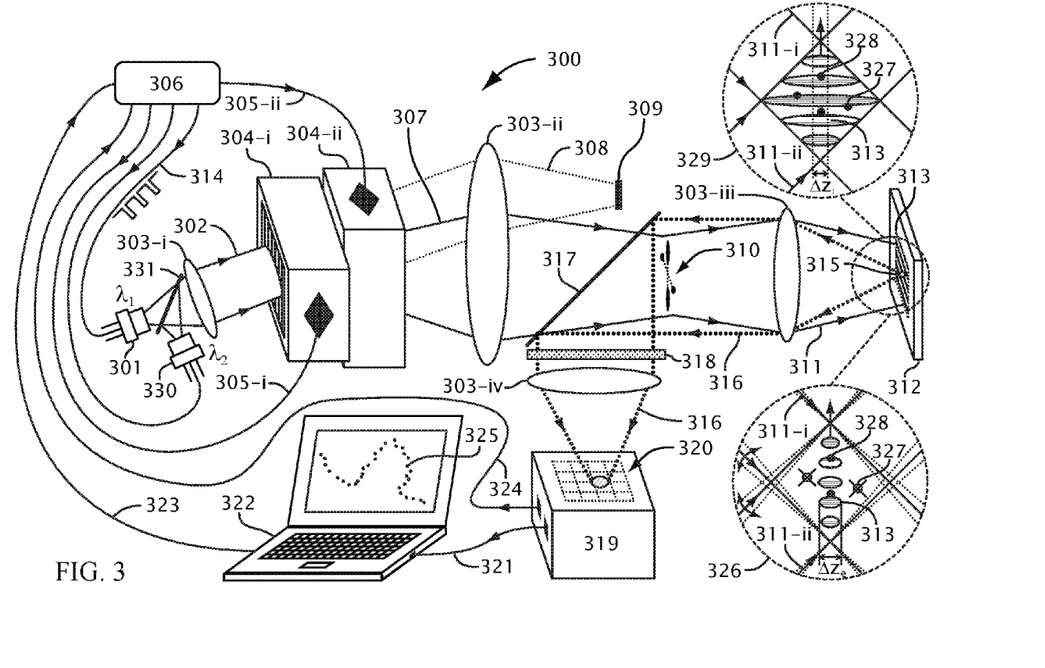
FIG. 3 illustrates a system for rapidly generating and precisely phase-shifting orthogonal excitation patterns using a coupled pair of acousto-optic Bragg cells and an amplitude-modulated illumination source. A simplified microscopy system for illuminating the specimen, filtering the response radiation from the excitation radiation, and detecting it using a camera are also illustrated. A computer is shown controlling the acousto-optic devices using an RF signal generator and receiving data from the camera. The system can perform optical sectioning using excitation with partial spatial coherence, the degree of which may be acousto-optically controlled, as well as localization with an extended depth of field using spatially coherent interference patterns.

FIG. 3 illustrates a system 300, which may be utilized to rapidly and precisely generate and translate excitation patterns varying along orthogonal directions, such as the patterns used in system 200 of in FIG. 2 for estimating a location of one or more microscopic emitters in a specimen. In system 300, a source 301 of radiation 302 with a wavelength $\lambda_1$ may be substantially collimated with a lens 303-i and may illuminate a pair of orthogonally-oriented acousto-optic Bragg cells 304-i and 304-ii. The Bragg cells may be driven with corresponding signals 305-i and 305-ii generated by a controller 306, each signal comprising one or more radio frequency (RF) tones, which may be in the MHz to GHz range, for example. At each Bragg cell, the corresponding signal 305-i or 305-ii may drive a transducer coupled to an optical crystal, generating a traveling index of refraction perturbation in the optical crystal. Each distinct RF tone comprising the signal may thus produce a distinct periodic traveling refractive perturbation component in the Bragg cell and the perturbation component may diffract the incident radiation 302 in a distinct direction. For example, a pair of RF tones driving one of the Bragg cells 304-i or 304-ii may cause the Bragg cell to diffract a pair of beams at different angles in the corresponding diffraction plane, such as excitation radiation beams 106 and 107 of FIG. 1.

In some embodiments, one of the orthogonally-oriented Bragg cells may be driven with a single RF tone to diffract a single beam, while the other Bragg cell may be driven with a signal comprising a pair of RF tones to diffract a pair of beams. A lens 303-ii may be used to focus the diffracted portion 307 and the undiffracted portion 308 of the radiation 302 at an intermediate plane, where the undiffracted portion 308 may be blocked using a mask 309. The diffracted beams 307 may form a corresponding set of spots 310 in the intermediate plane. The diffracted beams 307 may then be re-collimated and combined near the specimen 312 using another lens 303-*iii* to form the excitation radiation 311, such as radiation 105 of FIG. 1. In some embodiments the diffracted beams 307 may be coherent and may interfere to produce an excitation interference pattern 313, such as pattern 108 of FIG. 1, which may be traveling rapidly across the specimen due to the different RF Doppler shifts of the beams. In some embodiments, the radiation source 301 may be modulated in amplitude by the controller 306 using signal 314 with a synchronously-generated frequency at or near the difference frequency of the RF tones to stroboscopically slow down or stop the traveling interference pattern at a desired phase. In some embodiments the phase of the interference pattern may also or instead be controlled by the controller 306 adjusting the relative phases of the RF tones comprising the drive signal of the Bragg cell diffracting the pair of beams.

In some embodiments the controller 306 may comprise direct digital synthesis (DDS) technology, which may be capable of controlling the phase with the resolution of 14 bits, merely by way of example for reference. In some embodiments utilizing high-speed electronics, it may be possible to change the phase of the interference pattern 313 on a time scale of nanoseconds, as determined by the temporal period of the traveling acoustic perturbation in the Bragg cell crystal, and to change the frequency of the interference pattern on a time scale of microseconds, as determined by the time taken by the acoustic perturbation to traverse the optical beam 302. In some embodiments, the speed of controlling the phase, frequency, amplitude, and/or orientation of the excitation radiation pattern using the acousto-optic Bragg cells may be substantially faster than the detector exposure time for each intensity value measurement during the locating time interval, and precision and/or accuracy of control over the phase of the interference pattern may be substantially higher than the precision and/or accuracy of estimating the phase of the detector signal using a PSI process.

In some embodiments one or the other Bragg cell may be driven to diffract a pair of beams, generating an excitation interference pattern along one or the other orthogonal direction sequentially, as in some of the embodiments of system 200 in FIG. 2. In other embodiments, both Bragg cells may be driven with pairs of RF tones simultaneously, thereby diffracting four beams and illuminating the specimen with a combination of excitation interference patterns varying along multiple directions which may have different spatial periods, as in other embodiments of system 200 in FIG. 2. In some embodiments, the Bragg cells 304-*i* and 304-*ii* may be driven with signals 305-*i* and 305-*ii* comprising more than two RF tones and may each diffract more than two beams, forming a non-sinusoidal excitation interference pattern 313 at the specimen 312.

In FIG. 3, an active emitter 315 located in or on the specimen 312 may produce a response radiation 316 in response to the excitation radiation 311. The response radiation 316 may be collected by the lens 303-*iii*, may be spectrally separated from the excitation by a dichroic beam splitter 317, may pass through an additional excitation blocking filter 318, and may be imaged onto a camera 319 comprising a pixel array 320 by a lens 303-*iv*. In some embodiments the response radiation may be coherently scattered by the emitter and may be sufficiently separated from the excitation radiation using a non-dichroic beam splitter, which in some embodiments may be polarizing and may be combined with one or more polarization retarders in an optical isolator geometry to reduce photon losses and/or improve separation between excitation and response radiations. The detector signals 321 from the camera may be acquired by a computer 322, which may comprise the processor 124 of FIG. 1 or processor 214 of FIG. 2, for example. The computer may also command the controller 306 using signal 323 to generate the required sequence of excitation patterns 313, which may be synchronized with the detector read out using signal 324. The computer 322 may process the acquired detector signals in accordance with various embodiments of FIG. 1 and FIG. 2 to synthesize a super-resolved reconstruction 325 of features in the specimen 312.

In some embodiments one or both of the Bragg cells may be controlled to reduce the effective spatial coherence of the excitation radiation 311 in accordance with various embodiments of U.S. Pat. No. 8,848,200, incorporated herein by reference. For example the signal 305-*ii* driving Bragg cell 304-*ii* and comprising a pair of RF tones may be frequency-modulated with an RF modulation bandwidth $\Delta f$. In some embodiments the RF modulation may comprise a fast and repetitive frequency sweep, for example. The RF-modulated signal 305-*ii* may impart an angular diversity on the diffracted beams corresponding to a directional spread of the beam foci 310 in the intermediate plane, depending on the modulation bandwidth $\Delta f$, without affecting the phase of the interference pattern 313 but resulting in a reduced effective spatial coherence of the excitation illumination when the detector signal is integrated incoherently during the detector exposure time.

As illustrated in inset 326 in FIG. 3, the angular diversity of the interfering beams 311-*i* and 311-*ii* may result in a limited depth of field $\Delta z_e$ of the excitation interference pattern 313, the axial extent of which may correspond to the RF modulation bandwidth $\Delta f$. The limited depth of field due to limited effective spatial coherence may be utilized to reject background emission by active emitters, such as emitter 327, located outside of the depth of field, which may produce only a weakly modulated or an unmodulated signal at the detector, whereas active emitters, such emitter 328, may produce a strong detector signal modulation which may be used for localization. This form of depth selectivity utilizing limited spatial coherence may be known to some as optical depth sectioning using structured illumination (as may be described, for example, in Neil, M. A. A., Juskaitis, R. and Wilson, T., Optics Letters, vol. 22, 1997, incorporated herein by reference), and may be used for three-dimensional imaging.

In some embodiments the source 301 of excitation radiation may be a laser with substantial spatial coherence, whereas in other embodiments the source 301 may not be spatially coherent, and may comprise a light-emitting diode (LED), for example. In such embodiments using an LED, the radiation 302 may not be fully collimated and may comprise a diversity of angles incident on the Bragg cells. As long the diverse angles of incidence are within the angular acceptance range of the Bragg cells, the optical sectioning effect illustrated in inset 326 may be attained without applying additional RF modulation to one or both of the Bragg cells as described above.

In other embodiments the source 301 and excitation radiation 311 may have substantial spatial coherence, and the interference pattern 313 formed by beams 311-*i* and 311-*ii* may have an extended depth of field, as illustrated in inset 329. In embodiments forming an image of the active emitters on a detector array, the depth of field of the excitation radiation may exceed the depth of field $\Delta z_i$ of the imaging system, so that signals from active emitters inside and outside $\Delta z_i$, such as emitters 327 and 328, may be fully modulated by the excitation pattern. In such embodiments, although the image of emitter 327, for example, may be out of focus and more extended than the image of emitter 328, its location may be estimated without substantial loss of precision from the integrated modulated signals of the detector elements receiving its response radiation, if crosstalk due to neighboring active emitters is minimal or mitigated as in various embodiments of FIG. 1 and FIG. 2. This may be in contrast to existing image-based centroid-finding localization methods such as PALM and STORM, which may be limited in their ability and/or precision of localizing out-of-focus emitters, which may contribute to unwanted background fluorescence.

In some embodiments, to differentiate and/or suppress crosstalk between in-focus and out-of-focus active emitters, such as emitters 328 and 327 in inset 329, the effective spatial coherence of the excitation radiation 311 may be varied, in some cases during the locating time interval, by adjusting the bandwidth $\Delta f$ of the RF modulation of one or both of the Bragg cells 304-$i$ and 304-$ii$ in accordance with various embodiments of U.S. Pat. No. 8,848,200.

In some embodiments one or more additional radiation sources, such as source 330 producing radiation with a wavelength $\lambda_1$, may be using a dichroic beam splitter 331, for example. The additional sources may be utilized as emitter activation or de-activation sources, or may be used for multi-spectral localization using wavelength-specific acousto-optically generated excitation patterns, for example.

It should be apparent to those skilled in the art that FIG. 3 represents just one of many possible embodiments. In some embodiments the cascaded Bragg cells 304-$i$ and 304-$ii$ may be positioned in conjugate image planes of an optical system instead of adjacent to each other as shown. The Bragg cells may comprise crystal, glass, liquid, plastic, or another acousto-optic medium. In other embodiments the acousto-optic devices 304-$i$ and 304-$ii$ may comprise surface-acoustic-wave modulators, may reflect the incident radiation 302, and may diffract radiation 307 by means of a traveling surface wave instead of the traveling refractive index perturbation of the Bragg cell. The diffracted second radiation 307 may comprise the $1^{st}$ diffraction order and/or other diffraction orders, including the $0^{th}$ order. In some embodiments one or both of the acousto-optic devices may be utilized in the Raman-Nath diffraction regime instead of the Bragg diffraction regime, and the excitation interference patterns may be produced by $\pm 1^{st}$ diffracted orders generated using a single-tone signal rather than a multi-frequency signal, for example. In some embodiments the undiffracted $0^{th}$ order beam 308 may be blocked using a polarization-selective filter instead of a mask in an intermediate image plane. In some embodiments a single multi-dimensional acousto-optic device may be used wherein multiple traveling perturbations may travel in different directions instead of two cascaded acousto-optic devices, which in some embodiments may comprise a single acousto-optic crystal with two orthogonal bonded transducers.

In some embodiments the amplitude modulation may be accomplished by modulating the radiation source 301, by using a modulator, such as a shutter or an acousto-optic modulator, modulating the radiation 302, the diffracted radiation 307, or the response radiation 316 from the emitter, or alternatively by electronically modulating the detected signal. The amplitude modulation may be pulse-like, sinusoidal, or of another functional form. In some embodiments utilizing one or more fast RF detectors, or in other embodiments where symmetric diffracted orders, such as $\pm 1^{st}$ orders, may produce a stationary interference pattern, stroboscopic amplitude modulation may not be necessary. The RF modulation of a Bragg cell signal imparting partial spatial coherence may be non-monotonic and/or non-linear. In some embodiments the controller 306 controlling the acousto-optic devices 304-$i$ and 304-$ii$ and modulating the light source 301 may be on a circuit board internal to the computer, or may comprise several external devices.

The spectra of the drive signals 305-$i$ and 305-$ii$ may comprise multiple distinct frequencies or may be continuous and the resulting interference pattern 313 may be periodic or aperiodic. In some embodiments, for example, a drive signal may comprise two frequencies varying in opposite directions with time and the amplitude modulation signal 314 may comprise narrow pulses with a period exceeding the propagation time of the acoustic perturbation across the optical beam 302 to produce a chirped interference pattern 313 having a spatially-varying period. The chirped interference pattern may be varying sinusoidally only within a local neighborhood of the emitter 315, and the spatially-varying period may be used to disambiguate the estimated emitter location in accordance with some embodiments in U.S. Pat. No. 8,531,650, incorporated herein by reference.

In some embodiments one or more spatial light modulators such as a grating, a micromirror array, a liquid crystal array, or a grating light valve may be used in place of one or both acousto-optic devices to generate the excitation radiation distribution 313, which may comprise an interference pattern or a partially-coherent image of the spatial modulator structure. In some embodiments a different kind of spatial modulator, such as a tilting mirror, a micromirror array, a grating light valve, or a liquid crystal device, may be used to vary the phase gradient at the specimen 312 and control the effective coherence of the excitation radiation in place of an acousto-optic device.

Figure 4:
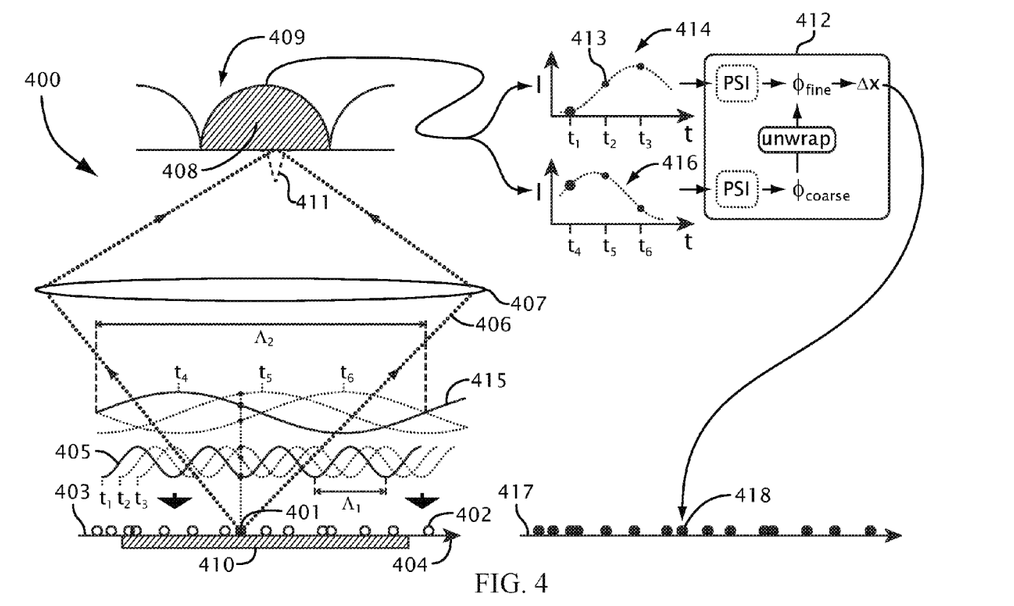
FIG. 4 illustrates a system and method for disambiguating the location of an emitter in embodiments where the detector may cover a region of the specimen spanning multiple periods of the excitation pattern. Disambiguation is accomplished by temporal phase unwrapping using excitation patterns with multiple spatial frequencies.

The optical imaging and illumination systems of FIG. 3. comprising lenses 303-$ii$, 303-$iii$, and 303-$iv$ and filters 317 and 318 may merely be a simplified embodiment for clarity of illustration. In another embodiment, for example, the source 301, acousto-optic devices 304-$i$ and 304-$ii$, beam block 309, and lenses 303-$i$, 303-$ii$, and 303-$iii$ may comprise an acousto-optic pattern generator module. In some embodiments the interference pattern 313 generated by the module may be optically relayed to a conjugate image plane of a microscope, which may comprise a variety of other optical elements, such as lenses, filters, beam splitters, and prisms, light sources, and mechanical elements, and may utilize an objective lens to illuminate the specimen 312 with activation and/or excitation radiations and to collect the response radiation, as in epi-fluorescence microscopy. In other embodiments, the pattern generator module may be used to illuminate the specimen from another direction without being optically coupled to the microscope FIG. 4 illustrates a system 400 for estimating a location of an active microscopic emitter, such as emitter 401, which may be interspersed among inactive emitters, such as emitter 402, in a specimen 403 along a direction 404. As in system 100 of FIG. 1, the emitter 401 may produce a response radiation to an excitation radiation pattern 405, and a portion of the response radiation 406 may be collected by a lens 407 and directed onto a detector element 408, which may in some embodiments be part of a detector array 409. In system 400, the detector 408 may be positioned to receive response radiations from a region 410 spanning multiple periods $\Lambda_1$ of excitation pattern 405, and may be substantially larger than the image 411 of the emitter 402. As in system 100 of FIG. 1, the excitation pattern 405 may be incrementally translated with respect to the specimen 403 during a locating time interval, and the location of the emitter 402 may be estimated by a processor 412 from the intensity values 413 of the resulting modulated detector signal 414 using a phase shifting interferometry (PSI) technique, for example. However, since the detector field of view region 410 spans multiple periods $\Lambda_1$ of the excitation pattern 405 and the phase of the detector signal $\varphi_{fine}$ may be estimated only modulo $2\pi$, the location estimate may be periodically ambiguous.

To unwrap the phase and disambiguate the emitter location, the specimen 403 may be illuminated with another excitation pattern 415 with a larger period $\Lambda_2$, which may exceed region 410 and may be incrementally translated to produce another detector signal 416. The excitation pattern 415 with period $\Lambda_2$ may be generated using system 300 of FIG. 4 by reducing the separation between the RF tones driving one of the Bragg cells, for example. The processor 412 may apply a PSI technique to detector signal 416 to produce a coarse phase estimate $\varphi_{coarse}$, which it may use to unwrap the fine phase estimate $\varphi_{fine}$ and disambiguate the location estimate of emitter 401, in accordance with methods which may be known as temporal phase unwrapping to those skilled in the art (see, for example, Huntley, J. M. and Saldner, H. O., Meas. Sci. Technol., vol. 8, 986-992, 1997, incorporated herein by reference). The disambiguated location estimate $\Delta x$, may then be used to populate a super-resolved reconstruction 417 of the specimen 403 with emitter representations 418 over the course of multiple locating time intervals during which different emitters may be activated, as in system 100 of FIG. 1.

It should be apparent to those skilled in the art that FIG. 4 represents just one of many possible embodiments. In some embodiments the period $\Lambda_2$ may be a multiple of period $\Lambda_1$. In other embodiments the period $\Lambda_2$ may be only slightly different from $\Lambda_1$ and a waveform with a larger period used for unwrapping may be synthesized computationally from the beating of the two detector signals, for example. In some embodiments, excitation patterns with periods $\Lambda_1$ and $\Lambda_2$ may be applied sequentially, whereas in other embodiments they may illuminate the specimen simultaneously and the coarse phase estimate $\varphi_{coarse}$ may be computed from a modulation envelope of the detector signal. In some embodiments the excitation pattern 415 may be an interference pattern comprising periods $\Lambda_1$ and $\Lambda_2$ formed coherently by a plurality of interfering beams. In some embodiments more than two excitation periods may be used to disambiguate the emitter location in a recursive fashion. In some embodiments different PSI techniques may be used to estimate $\varphi_{fine}$ and $\varphi_{coarse}$ and may utilize a different number of phase steps. One of the excitation patterns 405 and 415 may be translated after the other, or they may be generated and translated in an interleaved sequence. In some embodiments it may be possible to unwrap $\varphi_{fine}$ using only one or two phases of the coarse pattern 415 since the bias and modulation depth at each detector may be estimated using the fine pattern 405, and only a rough estimate of $\varphi_{coarse}$ may be needed for unwrapping.

Figure 5:
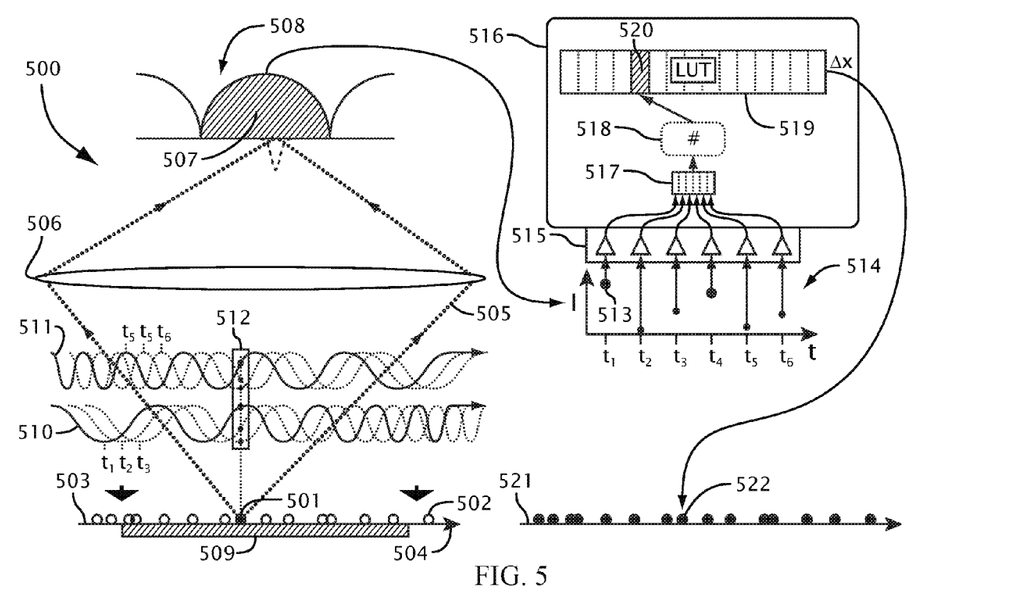
FIG. 5 illustrates a system and method for estimating a location of an active emitter using a sequence of potentially non-periodic excitation patterns, such as a combination of translated and flipped chirps, for example, which encode each resolvable location with a unique intensity modulation sequence at the detector. The location is decoded and estimated from the resulting detector signal intensity values using a lookup table instead of using an technique like PSI.

FIG. 5 illustrates a system 500 for estimating a location of an active microscopic emitter, such as emitter 501, which may be interspersed among inactive emitters, such as emitter 502, in a specimen 503 along a direction 504. As in system 100 of FIG. 1, the emitter 501 may produce a response radiation to an excitation radiation, and a portion of the response radiation 505 may be collected by a lens 506 and directed onto a detector element 507, which may in some embodiments be part of a detector array 508 and may be positioned to detect response radiations from region 509 on specimen 503. In system 500, the excitation radiation may comprise a sequence of non-periodic patterns, such as chirped patterns 510 and 511, which may be generated using system 300 of FIG. 3 by driving a Bragg cell with a fast double-sided chirp and strobing the radiation source once per Bragg cell access time, for example. In some embodiments, the patterns 510 and 511 may also be incrementally translated as illustrated.

During a locating time interval, each pattern and its translated versions may encode the emitter 501 with a unique temporal code 512 of excitation intensities corresponding to the emitter's location. For example, the temporal code 512 for emitter 501 produced by the 6 patterns in FIG. 5 (each chirped pattern shifted 3 times) may be unique to that location within region 509 of the specimen. The resulting intensity values 513 of the detector signal 514 may be digitized by a digitizer 515 and passed to a processor 516, which may combine the digitized intensity values to form a locating word 517. In some embodiments the processor may apply a hash function 518 to the locating word, which may translate the locating word into an address of a lookup table (LUT) 519. In other embodiments, the locating word 516 may address the LUT 518 directly. The LUT may comprise a unique mapping between temporal codes such as code 512 (processed by a hash-function in some embodiments) and locations at the specimen. For example, the addressed LUT memory cell 520 may contain the emitter location estimate $\Delta x$ with respect to a known reference in digital form (the center of region 509, for example). The decoded location estimate $\Delta x$, may then be used to populate a super-resolved reconstruction 521 of the specimen 503 with emitter representations 522 over the course of multiple locating time intervals during which different emitters may be activated, as in system 100 of FIG. 1.

It should be apparent to those skilled in the art that FIG. 5 represents just one of many possible embodiments. In some embodiments using non-periodic patterns, a LUT may not be needed to decode an emitter's location. For example, a single incrementally-translated chirped pattern, such as pattern 510, may produce a modulated detector signal which may be fitted to a sinusoidal function with its phase encoding a fine position of the emitter and its frequency encoding a coarse location of the emitter, in accordance with some embodiments of U.S. Pat. No. 8,531,650, incorporated herein by reference. In other embodiments, distinct non-periodic patterns may be used to uniquely encode the emitter location without translation. In some embodiments coarse non-periodic patterns may be used to disambiguate phase and location estimates computed using a PSI technique from a detector signal due to a translated periodic excitation pattern, such as pattern 405 of FIG. 4. In some embodiments the non-periodic patterns may be binary.

The digitizer 515 may be within a camera or a CMOS detector, for example, or may comprise an external digitizer, such as a digital oscilloscope. In embodiments utilizing a detector array, a separate LUT may be utilized for each detector element, or in cases where the mapping between the temporal code and the relative location $\Delta x$ may be replicated from pixel to pixel, a single LUT may be used. In some embodiments, the hashing function 518 may comprise a PSI technique, which may be applied to subsets of the measured intensity values. For example, for the illustrated patterns, the 3-step PSI technique of FIG. 1 may be applied to compute a phase from each triplet of intensity values produced by the respective shifted chirped patterns, such that a pair of phases may be computed for each active emitter. The phase of each chirp may vary quadratically across region 509, but in opposing directions, and for at least some locations within the region, such as the location of emitter 501, a unique mapping between the pair of computed phases and the location may exist and may be stored in the LUT 519. By using a pair of computed phase values instead of all 6 digitized intensity values to address the LUT, the size of the required LUT may be drastically reduced. In some embodiments, for outputs of the hash function 518 which may not map to a unique location, the corresponding LUT cell, such as cell 520, may contain a flag indicating that the mapping is not unique, which may be used to reject, modify, or qualify the location estimate in further processing.

Figure 6:
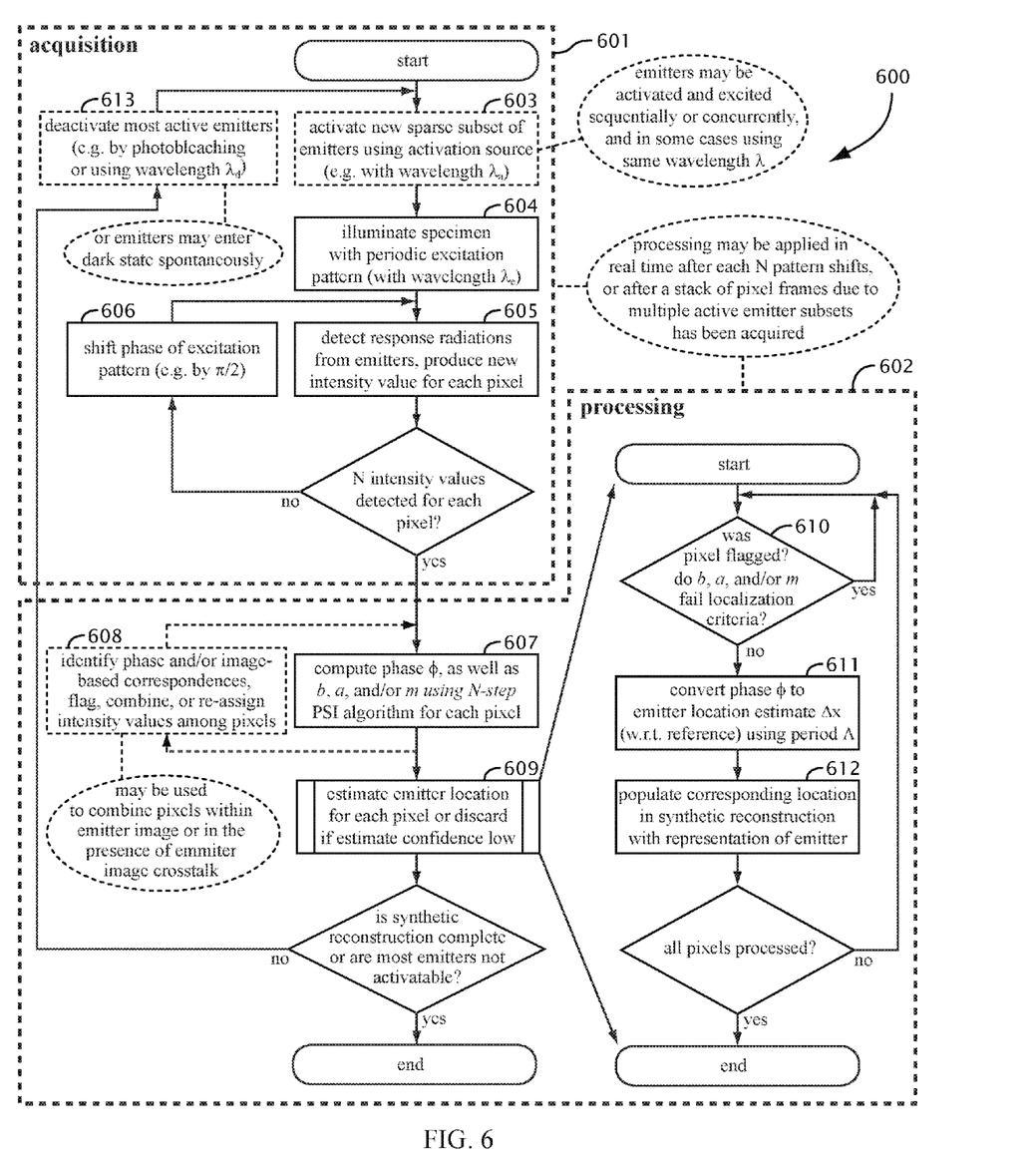
FIG. 6 is a flow chart illustrating a method of estimating locations of emitters in a microscopic specimen in embodiments using periodically-distributed phase-shifted excitation radiation and an array of detector pixels, and synthesizing a reconstruction of the specimen. The method may, for example, be performed in whole or in part within the systems of FIGS. 1-5.

FIG. 6 is a flow chart illustrating a method 600 of estimating locations of emitters in a microscopic specimen in embodiments using periodically-distributed phase-shifted excitation radiation and an array of detector pixels, and synthesizing a reconstruction of the specimen. The method 600 may, for example, be performed in whole or in part within the systems of FIGS. 1-5. Further aspects and additional embodiments of method 600 may be more thoroughly discussed within the provided descriptions of these figures and are thus not necessarily repeated here.

The method 600 may comprise acquisition steps shown in region 601 of the flow chart, and processing steps shown in region 602. The acquisition process may span a locating time interval and may begin with activating a spatially sparse set of emitters, which may be fluorescent, interspersed among a larger set of inactive emitters using an activation source with a wavelength $\lambda_a$, as provided in step 603. The specimen may then be illuminated with a periodic excitation pattern with a wavelength $\lambda_e$, such as pattern 108 of FIG. 1, causing each active emitter to emit a response radiation, such as fluorescence, in response to the excitation, as provided in step 604. In some embodiments the emitters may be activated concurrently with the excitation and steps 603 and 604 may be combined. In some embodiments the excitation illumination itself may also activate the emitters, as in the case of Alexa Fluor 647 fluorophores, for example, and a separate excitation source may not be required.

The response radiations from the emitters may then be detected by the pixel array, which may be exposed to an image of the specimen, producing an intensity value for each pixel, as provided in step 605. In some embodiments the strength of the activation source may be adjusted so that the probability of a pixel detecting response radiations from multiple active emitters is low. In some embodiments the exposure time of the pixel array may be set to maximize the detector signal, while comprising a fraction of the average emission time of an active emitter before it enters a dark state. Once the pixel array has been sufficiently exposed to the response radiations, the phase of the excitation pattern may be shifted as provided in step 606. In some embodiments the phase shift may be $\pi/2$, depending on the processing technique. In some embodiments, such as embodiments using the acousto-optic pattern generator of FIG. 3, the phase shift may be substantially instantaneous compared to the pixel integration time. The steps 605 and 606 may be repeated N times, where N is the number of steps used by the processing technique, to produce a signal at each pixel comprising N intensity values.

The processing steps may be implemented using a processor, such as processors 124 of FIG. 1, and may begin with computing a phase $\varphi$, as well as the bias b, amplitude a, and/or modulation depth m of the detected signal for each pixel using an N-step PSI technique from the detected intensity values, as provided in step 607 and described in FIG. 1, for example. In embodiments in which an image of an emitter spans multiple pixels and/or nearby emitters produce crosstalk, intensity values may be reassigned among pixels based on correspondences between the phases of neighboring emitters or based on intensity distribution in the pixel array image, as provided in step 608 and described in FIG. 1 and FIG. 2, for example, and step 607 may be applied to the reassigned intensity values. In some embodiments, signals from pixels receiving response radiation from the same emitter may be combined or flagged to prevent further processing. In some embodiments, steps 607 and 608 may be repeated multiple times until the computed quantities converge.

Once the PSI technique has been applied, each pixel may be evaluated and potentially processed to localize the corresponding emitter using the steps of sub-process 609. The bias b, amplitude a, and/or modulation depth m computed for the pixel in step 607, and any flags assigned to the pixel in step 608, may be utilized to assess whether the pixel should be processed further to localize a corresponding emitter, as provided in decision step 610. For example, low signal bias and/or modulation depth for the pixel may indicate the absence of an active emitter in the corresponding region of the specimen or a low localization confidence, whereas a high signal bias compared to other pixels may indicate multiple emitters. In such cases the pixel may not be processed further in some embodiments, or may require additional processing. If a pixel passes the localization criteria of step 610, the corresponding phase value may be converted in step 611 to a location with respect to a reference, such as the center of the specimen region corresponding to the pixel or the established location of another emitter, using the known spatial period of the excitation pattern and its phase $\varphi_{ref}$ at the reference. The estimated location may then be used to populate the corresponding location in the synthetic reconstruction of the specimen with a representation of the emitter, as described in FIG. 1, for example.

In embodiments applying the processing steps of region 602 in real time, when or by the time all pixels have been processed, some or all of the active emitters may be deactivated using another radiation source with a wavelength $\lambda_d$ or may be photobleached as provided in step 613, or may spontaneously enter a dark state, and the entire process in the flow chart may repeat for a new sparse subset of active emitters until the iterative specimen reconstruction is deemed sufficiently complete or most of the emitters can no longer be activated, due to photobleaching, for example. In other embodiments, the acquisition steps of region 601 may be repeated for multiple subsets of active emitters spanning multiple locating time intervals, and the resulting data may be accumulated before the full data stack is post-processed to synthesize the specimen reconstruction using the steps of region 602.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

It will be recognized by those of skill in the art that various modifications, alternative constructions, and equivalents may be used without departing from the spirit of the disclosed technology. By way of example, several such variations are set forth here, but this identification of potential variations is not intended to be exhaustive, and other variations will be evident for those of skill in the art.

For instance, while the optics have been described for particular types of systems in the illustrative embodiments, the principles of the disclosed technology may more generally be implemented with reflective optics, transmissive optics, or combinations thereof.

The arrangements illustrated in the drawings and described above are simple so that the principles of operation will be evident, but it will be appreciated that other systems may be implemented in a more complex fashion, such as by involving a greater number of lenses than shown and/or by involving additional conjugate optical planes. The lenses are illustrated merely by a way of an example and may represent other optical systems, which may include but are not limited to lenses, mirrors, prisms, beam splitters, gratings, gradient index lenses, diffractive lenses, or waveguides.

Although a single detector array has been described above for most embodiments, it will be understood that parallelized embodiments using multiple detector groups or arrays to look at different parts of the object, different spectral bands, different polarizations, etc. are also within the intended scope of the disclosed technology, and may be used in various embodiments where only a single detector array has been described. Moreover, the detector arrays may be located in a Fourier plane of the imaging optics rather than in the image plane, or in any other location allowing images of the object to be computed.

In some illustrative embodiments, only a pair of interfering beams has been shown, but the same principles typically also apply when many beams or when a continuous spatially modulated wavefront is diffracted. Such alternative embodiments are also within the intended scope of the disclosed technology.

In addition, the above elements may merely be a component of a larger system, wherein other rules may take precedence over or otherwise modify the application of the disclosed technology. Also, a number of steps may be undertaken before, during, or after the above elements are considered.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

he phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Accordingly, the above description should not be taken as limiting the scope of the disclosed technology, which is defined in the following claims.

What is claimed is:

1. A method for estimating a location of an emitter, the method comprising:
   (A) illuminating the emitter with an excitation radiation having a wavelength and a spatial distribution varying along at least one direction, the spatial distribution having at least one spatial period along the at least one direction, the emitter having a size smaller than the wavelength, and the emitter producing a response radiation in response to the excitation radiation;

(B) detecting at least a portion of the response radiation with a detector element producing a detector signal in response to the response radiation;
(C) changing the spatial distribution of the excitation radiation with respect to the emitter so as to cause a temporal modulation of the response radiation and of the detector signal, the temporal modulation comprising at least one temporal periodic component;
(D) estimating a phase of the at least one temporal periodic component of the detector signal; and
(E) estimating the location of the emitter from the phase estimated in (D) with a resolution finer than one quarter the wavelength.

2. The method of claim 1 wherein the emitter in (A) responds to a harmonic of the excitation radiation, and the location in (E) is estimated with a resolution finer than one quarter of the wavelength of the harmonic.

3. The method of claim 1 wherein the spatial distribution of the excitation radiation comprises a substantially periodic pattern and wherein changing the spatial distribution of the excitation radiation in (C) comprises translating the substantially periodic pattern with respect to the emitter.

4. The method of claim 3 wherein the excitation radiation in (A) comprises at least two illumination beams, and wherein translating the substantially periodic pattern comprises changing a phase relationship between the at least two illumination beams.

5. The method of claim 3 wherein illuminating the emitter in (A) comprises forming a substantially incoherent image of a structure, and wherein translating the substantially periodic pattern comprises translating the structure.

6. The method of claim 1 wherein estimating the at least one temporal periodic component of the detector signal in (D) comprises using a phase shifting interferometry process.

7. The method of claim 6 further comprising:
synthesizing a coarse periodic signal from a second period of the excitation radiation;
computing a phase of the coarse periodic signal from the detector signal; and
disambiguating the location of the emitter estimated in (E) using the phase of the coarse periodic signal.

8. The method of claim 1 further comprising:
computing at least one of a modulation depth of the detector signal and an amplitude of the detector signal.

9. The method of claim 8 wherein the excitation illuminating the emitter in (A) is substantially spatially incoherent, the method further comprising:
providing depth sectioning using the modulation depth of the detector signal.

10. The method of claim 8 further comprising:
estimating a confidence of the location estimate based on the at least one of the modulation depth of the detector signal and the amplitude of the detector signal.

11. The method of claim 8 further comprising:
estimating at least one of a size and an isolation of the emitter based on the at least one of the modulation depth of the detector signal and the amplitude of the detector signal.

12. The method of claim 1 wherein the excitation illuminating the emitter in (A) is substantially spatially coherent, and estimating the location of the emitter in (E) comprises estimating the location of the emitter within an extended depth of field.

13. The method of claim 1 wherein the emitter is a first emitter, the method further comprising:
forming a representation of the location of the first emitter with respect to at least one second emitter.

14. The method of claim 13 wherein the detector element is part of a detector array generating a plurality of detector signals in response to the response radiation and the method of claim 1 is applied to each of the plurality of detector element signals.

15. The method of claim 14 further comprising:
reassigning at least a portion of a first detector signal from a first detector element in the detector array to a second detector element in the detector array based on a correspondence between at least a portion of the first detector signal and at least a portion of a second detector signal from the second detector element.

16. The method of claim 1 wherein estimating the location of the emitter in (E) comprises estimating the location of the emitter in at least two dimensions.

17. A system for estimating a location of an emitter, the system comprising:
an illumination pattern generator to illuminate the emitter with an excitation radiation having a wavelength so as to cause the emitter to emit a response radiation, the emitter having a size smaller than the wavelength, the excitation radiation having a time-varying spatial distribution with at least one spatial period, and the response radiation having a temporal modulation comprising at least one temporal periodic component;
a detector to detect at least a portion of the response radiation, the detector configured to produce a detector signal in response to the response radiation; and
a processor, operably coupled to the detector, to (i) estimate a phase of the at least one temporal periodic component and (ii) estimate the location of the emitter from the phase with a resolution finer than one quarter of the wavelength.

18. The system of claim 17 wherein the illumination pattern generator comprises:
an acousto-optic device, in optical communication with a light source, to generate a plurality of excitation radiation beams interfering to produce the spatial distribution.

19. The system of claim 18 further comprising:
an amplitude modulator, in optical communication with the illumination pattern generator and/or operably coupled to the detector, to temporally modulate the amplitude of at least one of the excitation radiation, the response radiation, and the detector signal so as to stroboscopically control a spatial phase of the time-varying spatial distribution.

20. The system of claim 18 wherein the acousto-optic device is configured to impart a spatial gradient on the excitation radiation at the specimen, the gradient varying in time during an integration period of the detector to control a degree of spatial coherence of the excitation radiation.

21. A method for estimating a location of an emitter having a subwavelength size, the method comprising:
(A) illuminating the emitter with an excitation radiation having a wavelength and a spatial distribution varying along at least one direction, the emitter having a size smaller than the wavelength, and the excitation radiation causing the emitter to emit a response radiation;
(B) detecting at least a portion of the response radiation with a detector element producing a signal due to the detected response radiation;
(C) changing the spatial distribution of the excitation radiation so as to cause a temporal modulation of the excitation radiation at the emitter and produce a temporal modulation of the detector signal encoding the location of the emitter, the temporal modulation at the emitter being substantially non-periodic and substantially uncorrelated with respect to the temporal modulation at one or more other locations;

(D) decoding the detector signal to estimate the location of the emitter with a resolution finer than one quarter of the wavelength.

22. The method of claim 21 wherein decoding the detector signal in (D) comprises using a lookup table.

* * * * *